(12) United States Patent
Kim et al.

(10) Patent No.: US 9,407,055 B2
(45) Date of Patent: **\*Aug. 2, 2016**

(54) METHODS OF MODULATING MICROLASERS AT ULTRALOW POWER LEVELS, AND SYSTEMS THEREOF

(71) Applicant: CALIFORNIA INSTITUTE OF TECHNOLOGY, Pasadena, CA (US)

(72) Inventors: Seheon Kim, Pasadena, CA (US); Axel Scherer, Barnard, VT (US); Aditya Rajagopal, Irvine, CA (US); Chieh-Feng Chang, Pasadena, CA (US)

(73) Assignee: CALIFORNIA INSTITUTE OF TECHNOLOGY, Pasadena, CA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 14/684,280

(22) Filed: Apr. 10, 2015

(65) Prior Publication Data

US 2015/0222073 A1  Aug. 6, 2015

Related U.S. Application Data

(62) Division of application No. 13/764,620, filed on Feb. 11, 2013, now Pat. No. 9,031,102.

(60) Provisional application No. 61/605,462, filed on Mar. 1, 2012.

(51) Int. Cl.
  *H01S 3/06* (2006.01)
  *H01S 3/091* (2006.01)
  (Continued)

(52) U.S. Cl.
  CPC .............. *H01S 3/0627* (2013.01); *H01S 3/025* (2013.01); *H01S 3/091* (2013.01); *H01S 3/102* (2013.01); *H01S 3/1028* (2013.01); *H01S 3/115* (2013.01); *H01S 5/0612* (2013.01);
  (Continued)

(58) Field of Classification Search
  None
  See application file for complete search history.

(56) References Cited

U.S. PATENT DOCUMENTS 4,800,556 A  1/1989 Charlier et al.
4,825,081 A  4/1989 Wille et al.
(Continued)

FOREIGN PATENT DOCUMENTS

EP  0 053 790  6/1982
EP  0 386 965  9/1990
(Continued)

OTHER PUBLICATIONS

Non-Final Office Action issued for U.S. Appl. No. 14/306,813, filed Jun. 17, 2014 in the name of Axel Scherer et al. mail date: Oct. 2, 2014.
(Continued)

*Primary Examiner* — Joshua King
(74) *Attorney, Agent, or Firm* — Steinfl & Bruno LLP (57) ABSTRACT

A microlaser system includes an optical source, a microlaser, an actuator switch, and a photovoltaic power source. The microlaser, which includes a control element, is optically pumped by at least a portion of light emitted by the optical source. The actuator switch is configured to be activated by a triggering event. Furthermore, the photovoltaic power source is coupled in a series connection with the actuator switch and the control element, the series connection configured to connect the photovoltaic power source to the control element of the microlaser when the actuator switch is activated by the triggering event.

7 Claims, 11 Drawing Sheets

(51) Int. Cl.
*H01S 3/102* (2006.01)
*H01S 3/02* (2006.01)
*H01S 3/115* (2006.01)
*H01S 5/30* (2006.01)
*H01S 3/105* (2006.01)
*H01S 5/06* (2006.01)
*H01S 5/10* (2006.01)
*A61B 5/1459* (2006.01)

(52) U.S. Cl.
CPC ............ *H01S 5/3013* (2013.01); *A61B 5/1459* (2013.01); *H01S 3/105* (2013.01); *H01S 5/0607* (2013.01); *H01S 5/1042* (2013.01)

(56) References Cited

U.S. PATENT DOCUMENTS

| | | | |
|---|---|---|---|
| 5,291,502 | A | 3/1994 | Pezeshki et al. |
| 5,369,657 | A | 11/1994 | Cho et al. |
| 5,545,980 | A | 8/1996 | Nakamoto et al. |
| 5,629,951 | A | 5/1997 | Chang-Hasnain et al. |
| 6,255,976 | B1 | 7/2001 | Watanabe et al. |
| 6,437,554 | B1 | 8/2002 | Atwater et al. |
| 6,686,697 | B2 | 2/2004 | Cho et al. |
| 6,754,950 | B2 | 6/2004 | Furukawa et al. |
| 6,757,467 | B1 | 6/2004 | Rogers |
| 6,819,812 | B2 | 11/2004 | Kochergin et al. |
| 6,836,578 | B2 * | 12/2004 | Kochergin ......... G01D 5/35316 372/20 |
| 6,963,119 | B2 | 11/2005 | Colgan et al. |
| 6,970,619 | B2 | 11/2005 | Baumann et al. |
| 7,598,552 | B2 | 10/2009 | Park |
| 7,928,471 | B2 | 4/2011 | Mastro et al. |
| 7,965,948 | B1 | 6/2011 | Bugash et al. |
| 8,787,752 | B2 | 7/2014 | Scherer et al. |
| 9,031,102 | B2 | 5/2015 | Kim et al. |
| 2003/0090161 | A1 | 5/2003 | Marlow et al. |
| 2003/0099273 | A1 | 5/2003 | Murry et al. |
| 2004/0004751 | A1 | 1/2004 | Vilhelmsson |
| 2006/0046312 | A1 | 3/2006 | Kiesel et al. |
| 2007/0116082 | A1 | 5/2007 | Feve et al. |
| 2007/0187632 | A1 | 8/2007 | Igarashi |
| 2008/0039770 | A1 | 2/2008 | Francis et al. |
| 2008/0089367 | A1 | 4/2008 | Srinivasan et al. |
| 2009/0015141 | A1 | 1/2009 | Wang et al. |
| 2009/0159123 | A1 | 6/2009 | Kothari et al. |
| 2010/0008666 | A1 | 1/2010 | Kovsh |
| 2010/0084729 | A1 | 4/2010 | Steinbrueck et al. |
| 2011/0044694 | A1 * | 2/2011 | Scherer ................ A61B 5/6867 398/116 |
| 2012/0001149 | A1 | 1/2012 | Menon |

FOREIGN PATENT DOCUMENTS

| | | |
|---|---|---|
| EP | 0 451 992 | 10/1991 |
| JP | 05-243588 | 9/1993 |
| JP | 2001-250967 | 9/2001 |
| JP | 2004-363594 | 12/2004 |
| JP | 2006-266846 | 10/2006 |
| JP | 2006-267477 | 10/2006 |
| KR | 10-1999-0028493 | 4/1999 |
| KR | 10-0781545 | 12/2007 |
| KR | 10-0906270 | 7/2009 |

OTHER PUBLICATIONS

Final Office Action issued for U.S. Appl. No. 14/306,813, filed Jun. 17, 2014 in the name of Axel Scherer et al. mail date: Mar. 24, 2015.
Supplementary Search Report issued for European Patent Application No. EP 10810692.3 filed on Feb. 16, 2012 in the name of California Institute of Technology. mail date: Nov. 24, 2014.
Supplementary Written Opinion issued for European Patent Application No. EP 10810692.3 filed on Feb. 16, 2012 in the name of California Institute of Technology. mail date: Nov. 24, 2014.
Advisory Action issued for U.S. Appl. No. 13/764,620 filed in the name of Seheon Kim et al. on Feb. 11, 2013. Mail Date: Oct. 27, 2014.
Extended European Search Report Application No. 10810692.3 filed on Aug. 20, 2010 in the name of California Institute of Technology Mail Date: Nov. 24, 2014.
Final Office Action issued for U.S. Appl. No. 12/860,723, filed Aug. 20, 2010 in the name of Axel Scherer et al. Mail Date: Apr. 16, 2013.
Final Office Action for U.S. Appl. No. 13/764,620 filed in the name of Seheon Kim et al. on Feb. 11, 2013. Mail Date: Jul. 15, 2014.
Non-Final Office Action issued for U.S. Appl. No. 12/860,723, filed Aug. 20, 2010 in the name of Axel Scherer et al. Mail Date: Oct. 24, 2012.
Non-final office action for U.S. Appl. No. 13/764,620 filed in the name of Seheon Kim on Feb. 11, 2013. Mail Date: Feb. 20, 2014.
Notice of Allowance issued for U.S. Appl. No. 13/764,620 filed in the name of Seheon Kim et al. on Feb. 11, 2013. Mail Date: Jan. 20, 2015.
Notice of Allowance issued for U.S. Appl. No. 14/306,813 filed in the name of Axel Scherer et al. on Jun. 17, 2014. Mail Date: Jul. 21, 2015.
Notice of Allowance for U.S. Appl. No. 12/860,723, filed Aug. 20, 2010 in the name of Axel Scherer et al. Mail Date: May 12, 2014.
Notice of Allowance for U.S. Appl. No. 12/860,723, filed Aug. 20, 2010 in the name of Axel Scherer et al. Mail Date: Sep. 12, 2013.
Restriction Requirement issued for U.S. Appl. No. 12/860,723, filed Aug. 20, 2010 in the name of Axel Scherer et al. Mail Date: Jul. 31, 2012.
Restriction Requirement issued for U.S. Appl. No. 13/764,620, filed Feb. 11, 2013 in the name of Seheon Kim Mail Date: Sep. 20, 2013.
PCT International Search Report issued for PCT/US2010/046220 filed Aug. 20, 2010 in the name California Institute of Technology et al. Mail Date: Apr. 20, 2011.
PCT International Search Report and Written Opinion issued for PCT/US2013/025632 filed Feb. 11, 2013 in the name of California Institute of Technology Mail Date: May 16, 2013.
PCT Written Opinion issued for PCT/US2010/046220 filed Aug. 20, 2010 in the name California Institute of Technology et al. Mail Date: Apr. 20, 2011.
Andre, W., et al., Micro-photovoltaic Cells Designed for Magnetotaxis-based Controlled Bacterial Microrobots, IEICE Electronics Express, 2008, 5: 101-106.
Fujita, M., et al., *Continuous wave lasing in GaInAsP microdisk injection laser with threshold current of 40 µA*, Electron. Lett., 2000, vol. 36, pp. 790-791.
Hempler et al., *Pulsed Pumping of Semiconductor Disk Lasers*, Mar. 19, 2007, Optics Express, 15, 6, 3247-3256.
Inoshita, K. et al., *Fabrication of GaInAsP/InP photonic crystal lasers by ICP etching and control of resonant mode in point and line composite defects*, IEEE J. Sel. Top. Quantum Electron, 2003, vol. 9, pp. 1347-1354.
Mo, Y. et al., *Micro-machined gas sensor array based on metal film micro-heater*, Sensors and Actuators B, 2001, vol. 79, pp. 175-181.
Sadek, A.S. et al., *Wiring nanoscale biosensors with piezoelectric nanomechanical resonators*, Nano Lett., 2010, vol. 10, pp. 1769-1773.
Ushigome, R. et al., *GaInAsP microdisk injection laser with benzocyclobutene polymer cladding and its athermal effect*, Jpn. J. Appl. Phys., 2002, vol. 41, pp. 6364-6369.

* cited by examiner

METHODS OF MODULATING MICROLASERS AT ULTRALOW POWER LEVELS, AND SYSTEMS THEREOF

CROSS REFERENCE TO RELATED APPLICATIONS

The present application is a divisional of U.S. patent application Ser. No. 13/764,620, filed on Feb. 11, 2013, which, in turn, claims priority to U.S. Provisional Application No. 61/605,462, filed on Mar. 1, 2012 and entitled "Methods of Modulating Microlasers at Ultralow Power Levels and Related Devices," all of which are incorporated herein in their entirety by reference.

FIELD

The present teachings relate to microlasers. More specifically, the present disclosure relates to microlasers that can be incorporated into a variety of monitoring applications wherein low power consumption is desirable.

BACKGROUND

Figure 1:
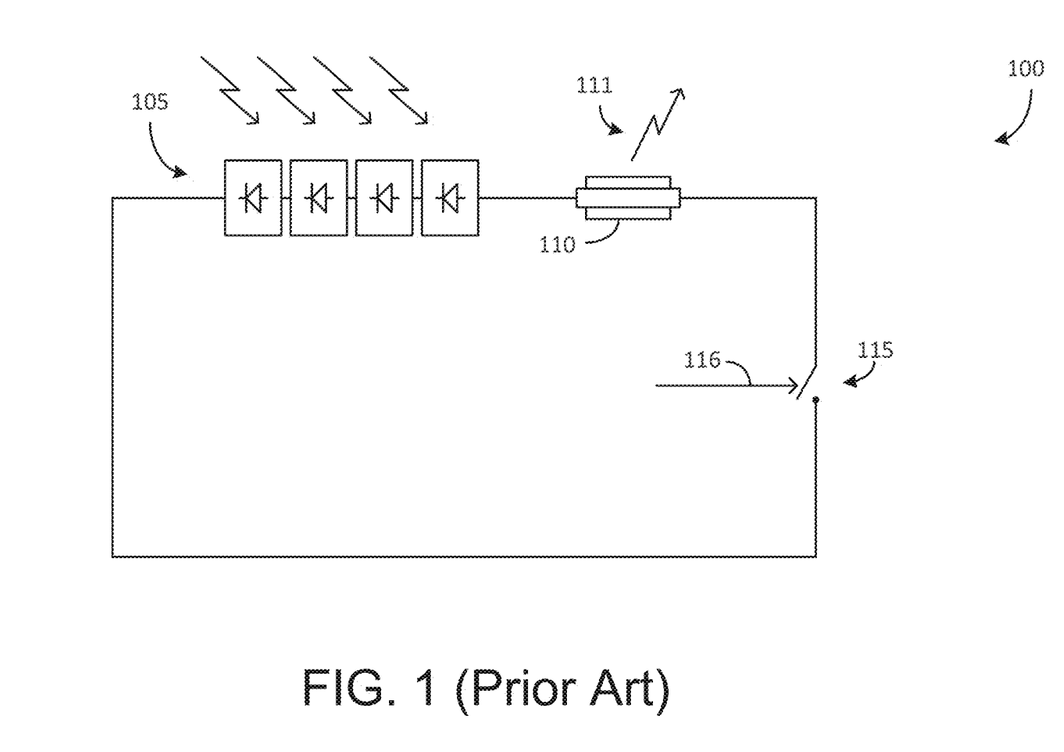
FIG. 1 shows a prior art microlaser system that includes a semiconductor microlaser arranged in a forward-biased configuration.

FIG. 1 shows a prior art microlaser system that includes a photovoltaic power source 105 for providing power via switch 115 to semiconductor microlaser 110 that is arranged in a forward-biased configuration.

When switch 115 is in an open condition, photovoltaic power source 105 is disconnected from microlaser 110, thereby placing microlaser 110 in an off state. However, when switch 115 is closed (as a result of a switch activation signal provided via line 116), photovoltaic power source 105 provides a voltage in the range of 1.5-2V to drive microlaser 110 into an on state and generate output laser beam 111.

The driving voltage (1.5-2V) required to turn on microlaser 110 is roughly ten times higher than what a single photovoltaic cell can generate in an open circuit condition. Consequently, the prior art arrangement shown in FIG. 1 necessitates a more complex and expensive photovoltaic power source 105 incorporating multiple photovoltaic cells in a tandem arrangement. Furthermore, the manner in which semiconductor microlaser 110 is operated proves inefficient in terms of power consumption.

SUMMARY

According to a first aspect of the present disclosure, a microlaser system includes an optical source, a microlaser, an actuator switch, and a photovoltaic power source. The microlaser, which includes a control element, is optically pumped by at least a portion of light emitted by the optical source. The actuator switch is configured to be activated by a triggering event. The photovoltaic power source is coupled in a series connection with the actuator switch and the control element, the series connection configured to connect the photovoltaic power source to the control element of the microlaser when the actuator switch is activated by the triggering event.

According to a second aspect of the present disclosure, a method of operation includes directing light upon a microlaser for optically pumping the microlaser; and detecting the occurrence of a triggering event based on a change in an optical output of the microlaser, the change in optical output occurring in response to connecting a photovoltaic power source to the microlaser only upon occurrence of the triggering event.

According to a third aspect of the present disclosure, a method of operation includes directing light upon a microlaser for optically pumping the microlaser; and connecting a photovoltaic power source to modify an operational condition of the microlaser only upon occurrence of a triggering event, the modified operational condition indicative of the occurrence of the triggering event.

Further aspects of the disclosure are shown in the specification, drawings and claims of the present application.

BRIEF DESCRIPTION OF THE DRAWINGS

The accompanying drawings, which are incorporated into and constitute a part of this specification, illustrate one or more embodiments of the present disclosure and, together with the description of a few example embodiments, serve to explain the principles and implementations of the disclosure. The components in the drawings are not necessarily drawn to scale. Instead, emphasis is placed upon clearly illustrating various principles. Moreover, in the drawings, like reference numerals designate corresponding parts throughout the several views.

DETAILED DESCRIPTION

Throughout this description, embodiments and variations are described for the purpose of illustrating uses and implementations of the inventive concept. The illustrative description should be understood as presenting examples of the inventive concept, rather than as limiting the scope of the concept as disclosed herein.

The various embodiments described herein are generally directed at a microlaser system that may be used in various monitoring applications, including applications involving detection of one or more occurrences of an event. The microlaser system incorporates a microlaser which is optically pumped into operation based on photoluminescence by a light source (thereby avoiding a power penalty associated with using a separate power source, such as a photovoltaic cell). The microlaser emits a laser beam when pumped into operation by the light source.

The microlaser system further incorporates an event sensor circuit that provides a trigger signal to a switch. When a triggering event occurs, the switch is activated by the trigger signal, and a photovoltaic power source is coupled to a control element of the microlaser. When energized by the photovoltaic power source, the control element (which can be implemented in a variety of ways, some of which are described below) operates to cause a change in characteristic (wavelength, intensity etc.) of the emitted laser beam. This change in characteristic (which may be alternatively understood as modulation of an emitted laser beam) may be used to optically communicate the occurrence of the event.

Significantly, rather than using the photovoltaic power source to provide an electrical voltage/current (power) to drive the microlaser in the manner indicated in prior art FIG. 1, the photovoltaic power source is used to provide power for driving the control element instead. The power consumption of the control element is low enough to permit a relatively small photovoltaic power source to be used, thereby providing cost and efficiency benefits over prior art systems that use complex, higher capacity, and expensive photovoltaic power sources.

Four types of control elements and the corresponding changes in characteristics of the emitted laser beam are described below in accordance with the invention. In broad terms, the four types of control elements enable modulation of the emitted laser beam on the basis of temperature variation, piezoelectric deformation, capacitance variation, and electronic forward/reverse biasing of the microlaser.

Figure 2:
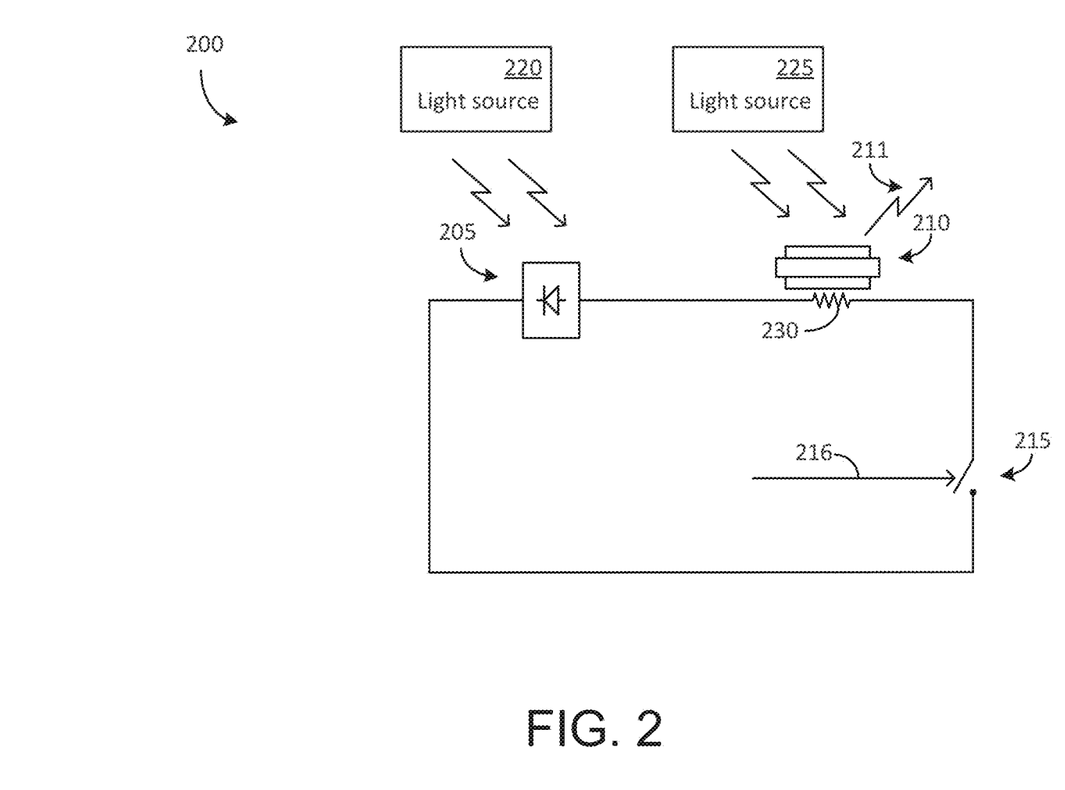
FIG. 2 shows a first embodiment of a microlaser system incorporating a temperature-based control element in accordance with the present disclosure.

To elaborate upon these aspects in more detail, attention is first drawn to FIG. 2, which shows a first embodiment of a microlaser system 200 based on varying the temperature of a microlaser whereby a wavelength shift and/or an intensity change is impressed upon an emitted beam of light. Microlaser system 200, which can be used for detecting various types of event occurrences (triggering events) in a wide variety of applications, includes microlaser 210 that is optically pumped into operation based on photoluminescence by a light source 225.

As can be understood, unlike prior art systems wherein a photovoltaic power source containing a significant number of photovoltaic cells is needed to drive a microlaser, in the embodiment shown in FIG. 1, photovoltaic power source 205 can be a low power source that generates low 'open circuit voltage' and current. More particularly, the open circuit voltage which is used to drive a control element (rather than the microlaser itself), is around 0.5 V, which is about 4 times smaller than what is required in prior art systems.

In the example embodiment shown in FIG. 2, the control element is a heater element, more particularly a micro-heater 230. Other types of control elements will be described below using other embodiments. Micro-heater 230 is in contact with a surface of microlaser 210, for example, a bottom surface of microlaser 210, such that heat provided by micro-heater 230 affects the active layer (not shown) of microlaser 210 and consequently changes a wavelength and/or an intensity of emitted beam 211.

A photovoltaic power source 205, which is configured to receive light from light source 220, convert the received light into electrical power, and provide the electrical power to micro-heater 230 when actuator switch 215 is in a closed (on) position. Actuator switch 215 is turned on/off (closed/open) on the basis of a trigger signal provided on line 216. The trigger signal is derived from an event sensor circuit (not shown) that is selected on the basis of various applications. In one example implementation, event detection system 200 is partially or entirely embedded inside an animate object (such as a human being for example), and used to detect the occurrence of various biomedical events, such as for example, when an undesirable substance carried in the bloodstream of the animate object exceeds a threshold level.

Furthermore, in this example embodiment as well as other embodiments described herein, light sources 220 and 225 may be combined into a single light source, a laser for example. In the example biomedical implementation described above, such a laser may be also embedded into the animate object for providing light to photovoltaic power source 205 and microlaser 210. The emitted beam 211 from microlaser 210 may be observed through suitable viewing ports provided in the animate object, or by using optical fiber to optically transport emitted beam 211 out of the animate object.

Micro-heater 230 may be implemented in a variety of ways. In one example implementation based on platinum/titanium (Pt/Ti) [3], micro-heater 230 can be selected to provide a localized temperature of around 150° C. when provided with 2.25 mW of driving power (0.75V×3 mA) from photovoltaic power system 205. At a driving power of 1 mW (0.5V×2 mA), the localized temperature can reach 75° C.

Figure 3:
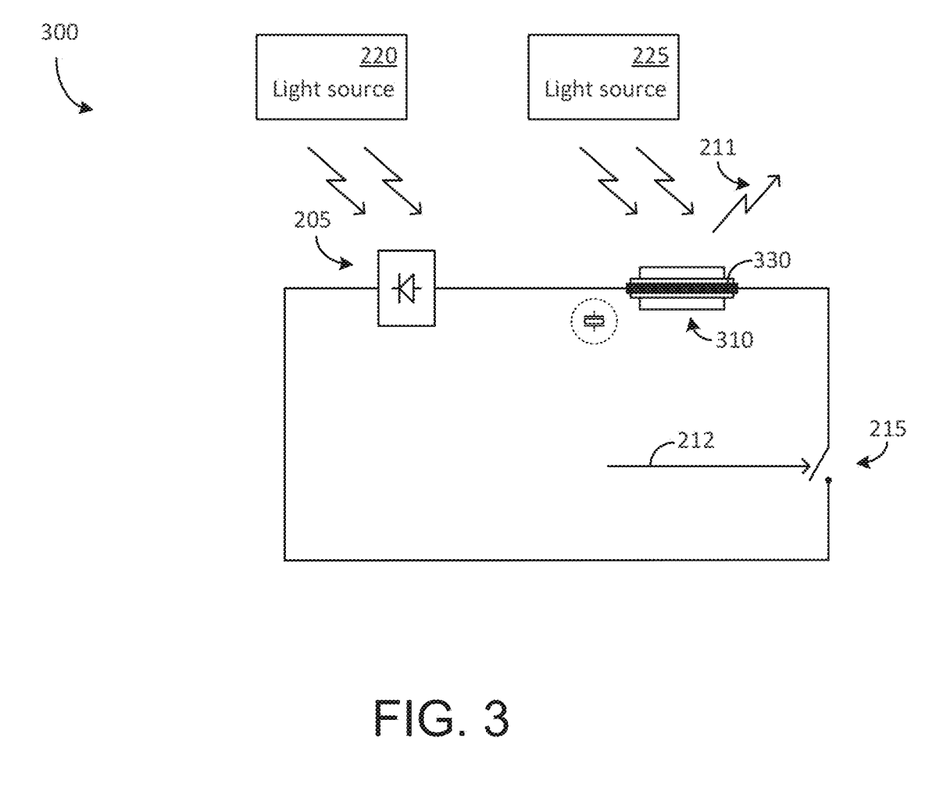
FIG. 3 shows a second embodiment of a microlaser system incorporating a piezoelectric-based control element in accordance with the present disclosure.

Attention is next drawn to FIG. 3, which shows a second embodiment of an event detection system 300 based on piezoelectric deformation of a portion of microlaser 310. The piezoelectric deformation results in a wavelength shift and/or an intensity change in an emitted beam of light. More particularly, in contrast to micro-heater 230 which is the control element in the first example embodiment, in this example embodiment, the control element is a piezoelectric layer 330 that may be fabricated as an integral layer inside microlaser 310. Piezoelectric layer 330 is a p-i-n doped layer that can be actuated by application of a low voltage under a reverse biased condition.

In one example implementation, piezoelectric layer 330 is significantly deformed when photovoltaic power system 205 provides a few hundred millivolts. This mechanical deformation causes emitted beam 211 to undergo a change in wavelength—either an increase or a decrease in wavelength depending on the way microlaser 310 is fabricated. The electrical power provided by photovoltaic power system 205 for enabling this wavelength change is as low as a few nW because there is essentially no current flow through microlaser 310 that is configured to operate in a reverse biased state (by suitable polarity-based connections between microlaser 310 and photovoltaic power system 205).

Figure 4:
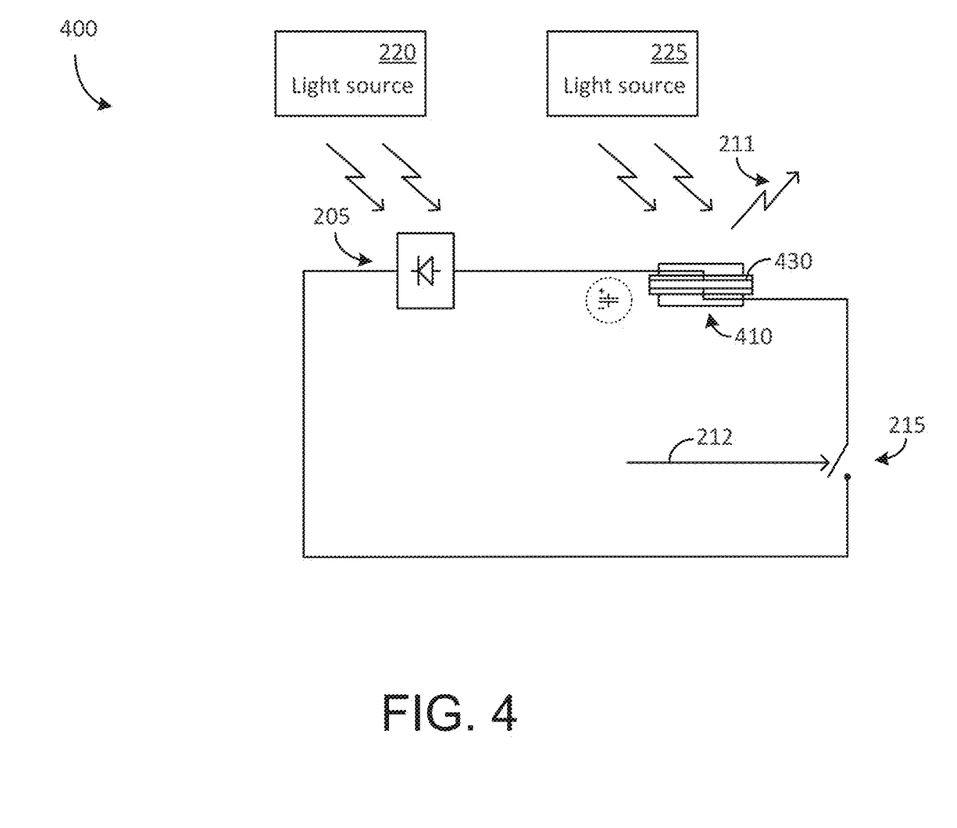
FIG. 4 shows a third embodiment of a microlaser system incorporating a capacitor-based control element in accordance with the present disclosure.

FIG. 4 shows a third embodiment of an event detection system 400 based on varying a capacitive element 430 that is a part of microlaser 410. In one example implementation, capacitive element 430 is a metallic membrane located above an active layer (described below in more detail using FIG. 8) of microlaser 410. The metallic membrane is deflected closer to a lasing disk upon application of a voltage provided by photovoltaic power system 205. The deflection results in an increase in light scattering by the metallic membrane and/or absorption of light in the metallic membrane and switches off microlaser 410.

In another example implementation, a thin insulating layer separates two micro-disks (described below in more detail using FIG. 9) that operate as a lasing cavity. The separation distance between the two micro-disks can be changed by electrostatic deflection of one or both of these two micro-disks upon application of a voltage provided by photovoltaic power system 205. The change in separation distance in microlaser 410 is intended as a means to alter a quality factor of the microlaser (in other word, Q-switching) and/or a resonant wavelength of the microlaser. As a result, wavelength/intensity of emitted beam 211 can be modulated in response to the triggering signal 212. The power provided by photovoltaic power system 205 for enabling this action is quite low because there is essentially no current flow through microlaser 410 that is configured to operate in a reverse biased state by suitable polarity-based connections between microlaser 410 and photovoltaic power system 205.

Figure 5:
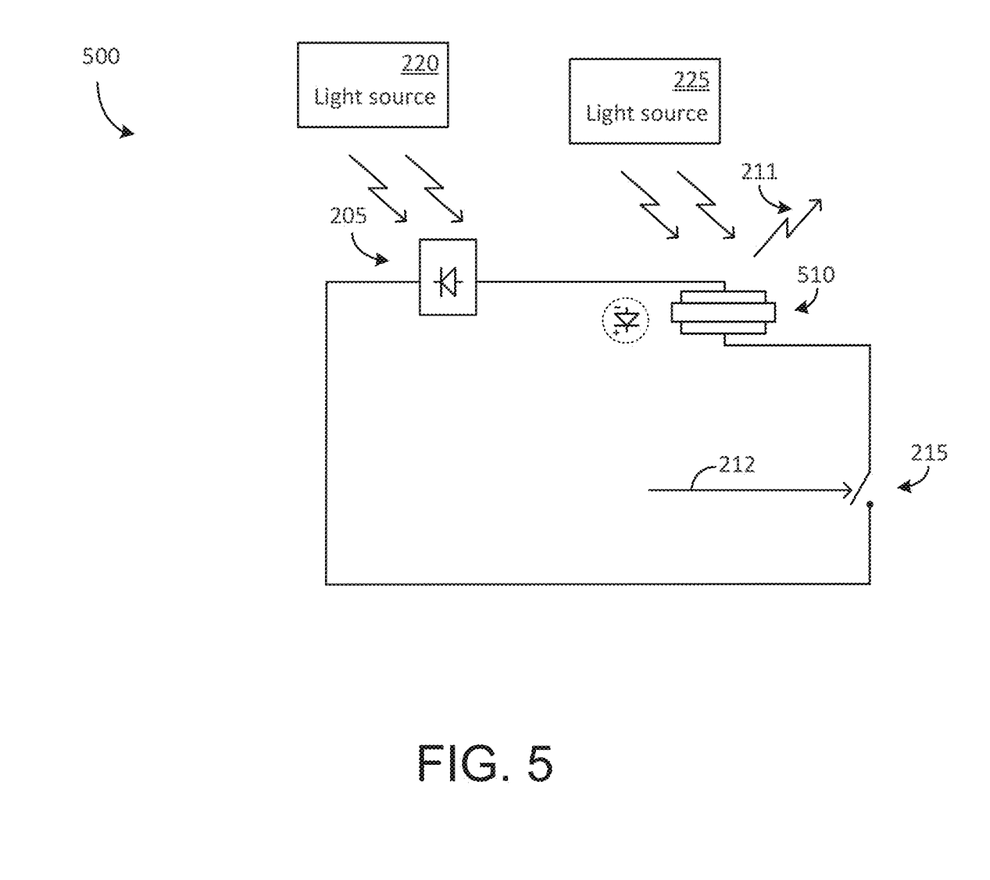
FIG. 5 shows a fourth embodiment of a microlaser system incorporating a reverse biased diode-based control element in accordance with the present disclosure.

FIG. 5 shows a fourth embodiment of an event detection system 500 based on electronic reverse biasing of microlaser 510, which may be interpreted as integrally incorporating a reverse-biased diode assembly. The electronic reverse biasing, which is carried out by suitable polarity-based connections between microlaser 510 and photovoltaic power system 205, is operative to changing the carrier concentration within microlaser 510. In this embodiment, light source 225 provides enough light to optically pump enough carriers within microlaser 510 so as to exceed a lasing threshold. An electrostatic field can be used to move carriers inside microlaser 510. In this approach, the carrier depletion close to the active lasing material inside microlaser 510 results in turning off microlaser 510. The resulting on-off binary nature of the emitted beam 211 can be used to carry digital information optically. The electrical power provided by photovoltaic power system 205 is quite low because there is essentially no current flow through microlaser 510 that is configured to operate in the reverse biased state.

In an alternative approach, in lieu of the reverse bias, a forward bias can be used to supply more carriers inside microlaser 510 so as to increase a laser gain. In this approach, light source 225 provides a stationary laser gain within microlaser 510 at a level close to/above a lasing threshold of the microlaser 510, which results in stationary laser emission 211 whose intensity does not change in time. Intensity of the emitted beam 211 can be modulated (increased) in response to the forward biased current by the photovoltaic power system 205. The electrical power provided by photovoltaic power system 205 for enabling this action is relatively low in comparison to prior art implementations.

Figure 6A:
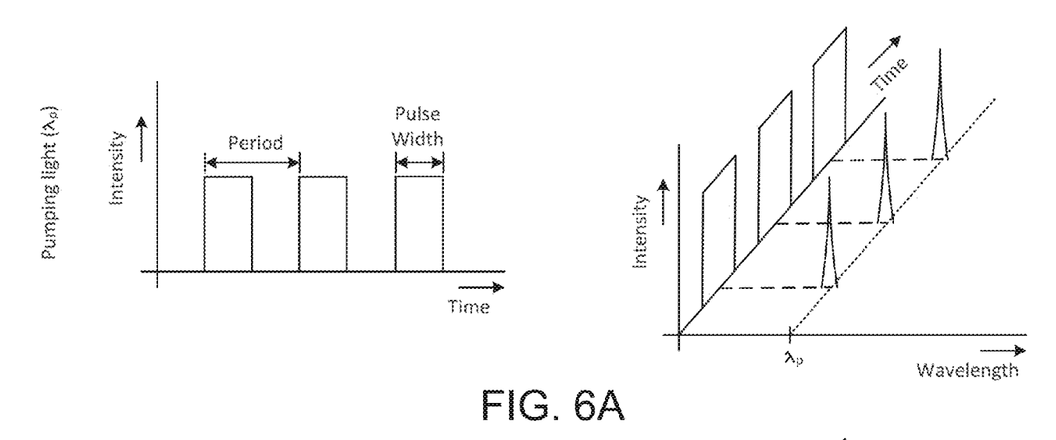
FIGS. 6A and 6B show graphs depicting a time profile of intensity and wavelength of a pump light (an emitted beam) in accordance with the present disclosure.

Attention is next drawn to FIG. 6A which shows a train of optical pulses provided by pump light source 225 to wirelessly power any of the microlaser embodiments described above. The train of optical pulses can be characterized by using a variety of parameters such as, a pulse period, a pulse width, a duty cycle, and/or a repetition rate. One or more of these parameters may be varied in accordance with one or more respective applications. For example, in a biological application where it is undesirable to overheat biological samples, it may be preferable to use pulse widths in the range of tens of nanoseconds. However, in certain other applications this low pulse width may not be suitable and consequently, a larger pulse width may be selected.

As for duty cycles, microlasers can be operated at duty cycles of 1% to 10% when a pulse period is in the range of 0.1 is to a few µs. Some advanced microlasers having ultra-low thresholds may be operated continuously (100% duty cycle) without encountering thermal problems. Peak power to operate a microlaser is typically about 1 kW/cm$^2$. About 10-20% of the pump light power 225 incident on some microlasers may be absorbed by the microlasers and used to create population inversion in the active layer.

FIG. 6A further shows a graph of light intensity versus wavelength (in other words, 'spectrum'), wherein wavelength $\lambda_p$ represents the wavelength of the light provided by light source 225 to wirelessly power any of the microlaser embodiments described above. In certain embodiments, this wavelength may not only be used by light source 225 but by light source 220. As indicated above, these two light sources may be implemented as a merged, single light source.

Figure 6B:
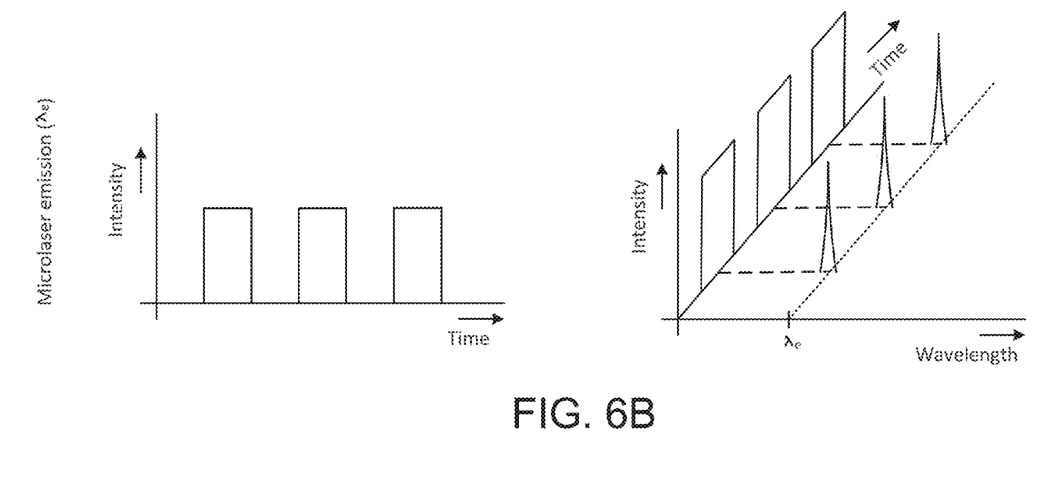

FIG. 6B shows a train of emitted beam pulses 211 from the microlaser embodiments described above. The train of microlaser output pulses is synchronized with that of the pump laser 225. The microlaser 211 is operated at a wavelength of $\lambda_e$, which is longer than that of the pump light wavelength $\lambda_p$. In the absence of a triggering 'event' 212, the peak output intensity and the emission wavelength $\lambda_e$ do not change in time.

Figure 7A:
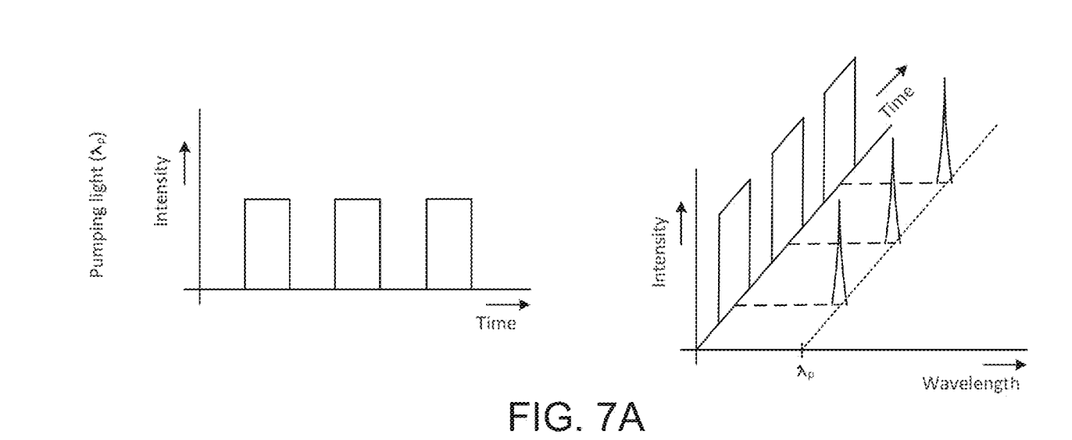
FIGS. 7A and 7B show graphs depicting a time profile of intensity and wavelength of a pump light (an emitted beam) in accordance with the present disclosure.

FIG. 7A shows a train of optical pulses that is provided by light source 225 at a wavelength of $\lambda_p$ to wirelessly power any of the microlaser embodiments described above. FIG. 7A further shows a graph of wavelength versus time. As can be understood, the wavelength of $\lambda_p$ remains unchanged over time regardless of the presence of an event (which would close actuator switch 215 but could not affect the pump light source 225).

Figure 7B:
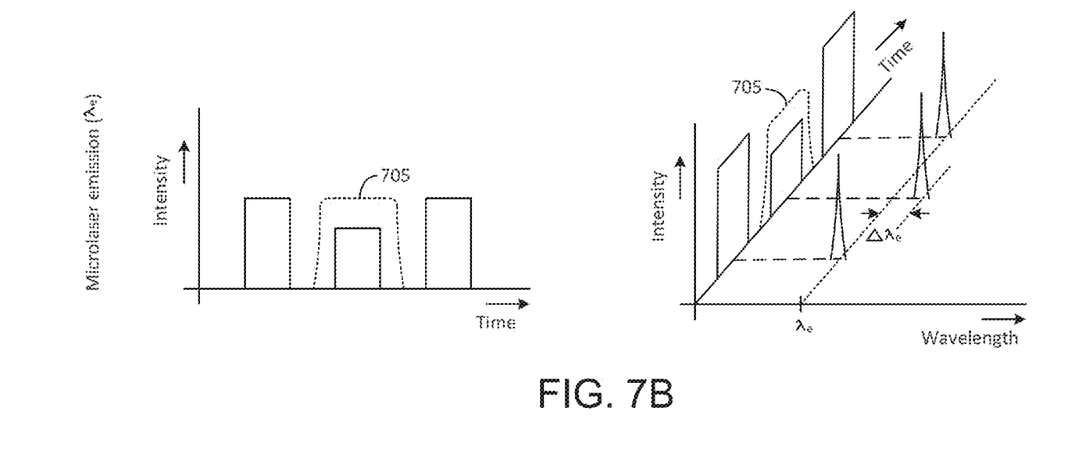

On the other hand, FIG. 7B illustrates a change in the time profile 705 of the event as a result of the occurrence of the event. The change in time profile 705 is characterized by a change in the intensity of emitted beam 211 in accordance with certain embodiments of the invention. In these and/or embodiments, a change in the wavelength ($\Delta\lambda_e > 0$ or $<0$) of emitted beam 211 may take place along with the intensity change as indicated in the graph of wavelength versus time.

Figure 8:
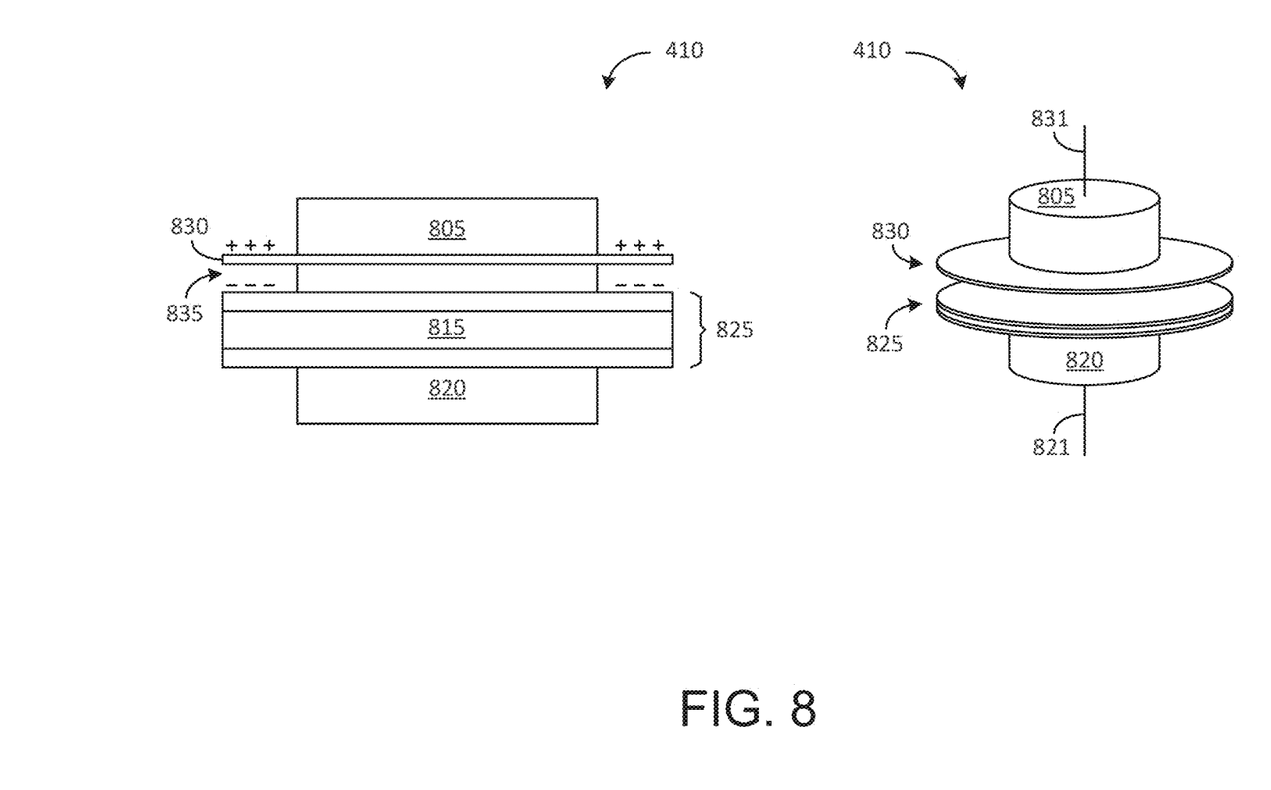
FIG. 8 shows some structural details of a microlaser incorporating a first embodiment of the capacitor-based control element in accordance with the present disclosure.

FIG. 8 shows some structural details of a microlaser 410 incorporating a first embodiment of the capacitor-based control element in accordance with the present disclosure. In this embodiment, capacitive element 430 (shown in FIG. 4) is a metallic membrane 830 separated by a gap 835 from lasing structure 825, which includes an active layer 815. Metallic membrane 830 is deflected closer to active layer 815 upon application of a voltage that is provided by photovoltaic power system 205 (shown in FIG. 4). The deflection results in an increase in light scattering by the metallic membrane and/or absorption of light in the metallic membrane and switches off microlaser 410. Layers 805 and 820 are configured as electrodes located on opposing sides of lasing structure 825 for application of the voltage by photovoltaic power system 205.

Figure 9:
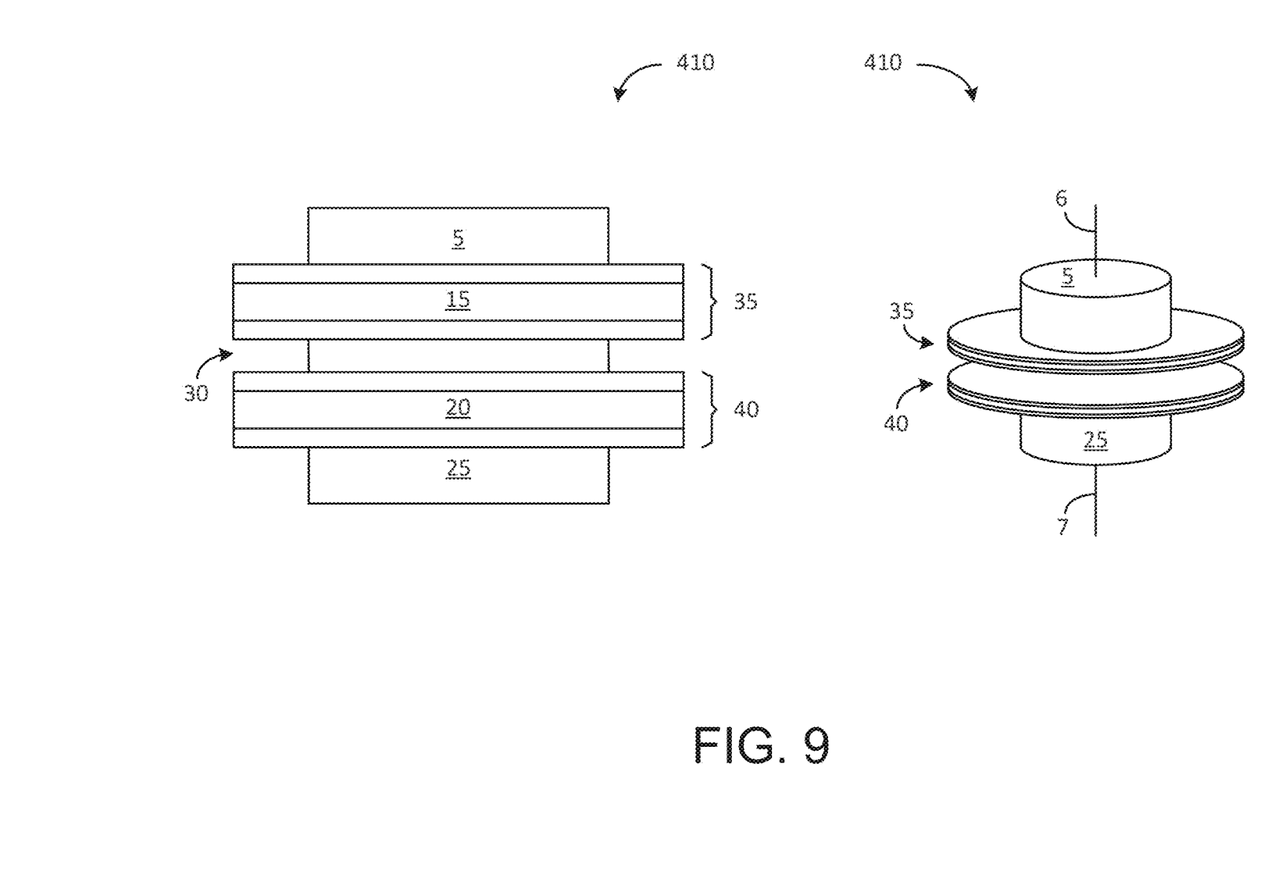
FIG. 9 shows some structural details of a microlaser incorporating a second embodiment of the capacitor-based control element in accordance with the present disclosure.

FIG. 9 shows some structural details of a microlaser 410 incorporating a second embodiment of the capacitor-based control element in accordance with the present disclosure. In this embodiment, capacitive element 430 is formed of an insulating layer 30 separating two micro-disks 35 and 40 (having active layers 15 and 20 respectively). The separation distance between the two micro-disks can be changed by electrostatic deflection of one or both of these two micro-disks upon application of a voltage (provided by photovoltaic power system 205). The change in separation distance causes microlaser 410 to be detuned out of the gain region, thereby resulting in a change in wavelength/intensity of emitted beam 211.

Figure 10:
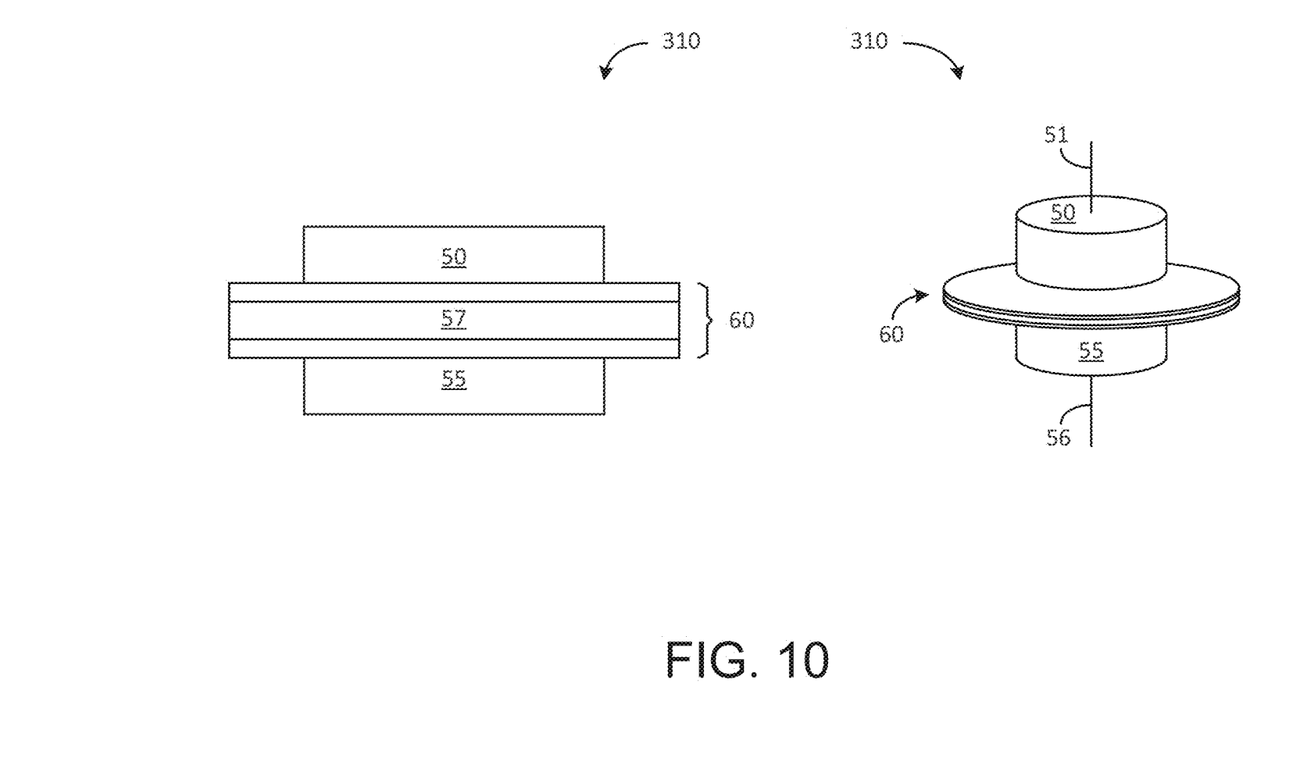
FIG. 10 shows some structural details of a microlaser incorporating the piezoelectric-based control element in accordance with the present disclosure.

FIG. 10 shows some structural details of a microlaser 310 incorporating the piezoelectric-based control element in accordance with the present disclosure. Microlaser 310 includes a pair of electrodes 50 and 55 that are located on opposite surfaces of layered structure 60, which includes multiple p-i-n layers. An intrinsic layer 57 serves as both an active layer and a piezoelectric layer. Under a reverse bias condition, the voltage applied via electrodes 50 and 55 induces mechanical stress in intrinsic layer 57 based on the piezoelectric nature of this layer. The mechanical stress causes the brim of layered structure 60 to deform, which in turn changes the emission wavelength ($\lambda_e$) of the emitted beam 211 (shown in FIG. 3). The change in wavelength is typically of the order of a few nanometers.

Figure 11:
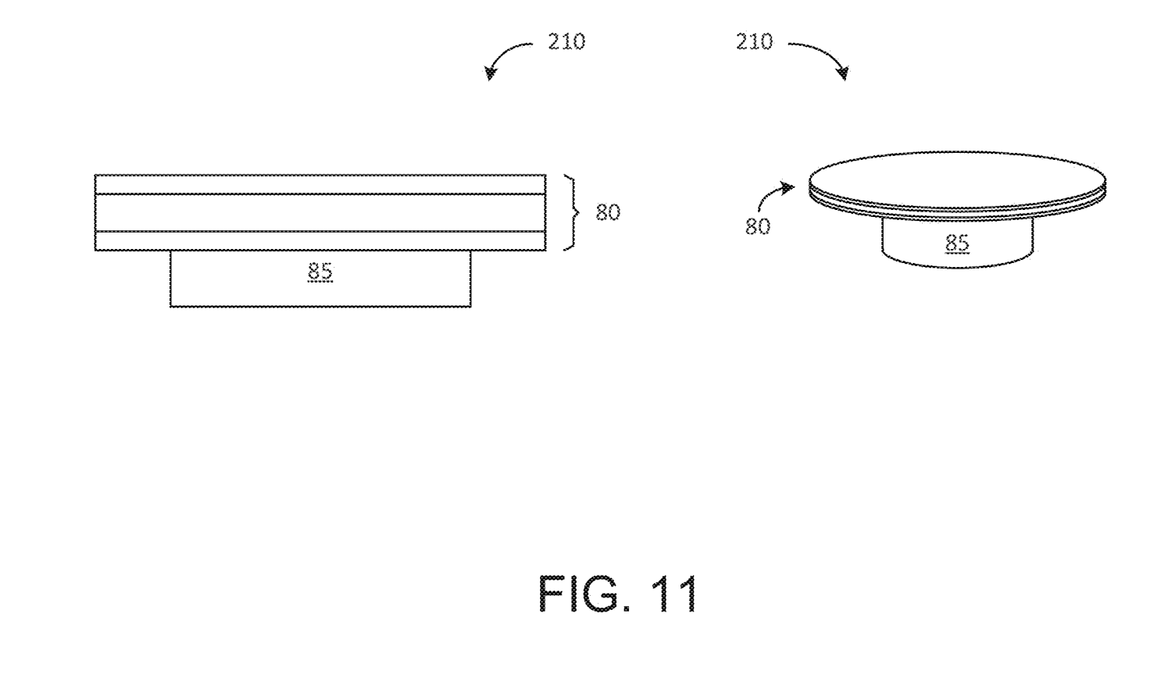
FIG. 11 shows some structural details of a microlaser incorporating the temperature-based control element in accordance with the present disclosure.

FIG. 11 shows some structural details of a microlaser 210 incorporating the temperature-based control element in accordance with the present disclosure. Microlaser 210 includes a metal pedestal 85 that is in contact with a microlaser layer 80. In some example implementations, metal pedestal 85 is made of one or more metals such as gold and platinum. Such metals operate as very good thermal as well as electrical conductors. Heat generated by heater 230 (shown in FIG. 2), which may be located inside metal pedestal 85 or external to metal pedestal 85, is efficiently delivered to microlaser layer 80 via metal pedestal 85. In one embodiment, where emitted beam 211 operates at a wavelength of 1.3 μm, microlaser layer 80 may incorporate an indium gallium arsenide phosphate (InGaAsP) compound. The diameter of microlaser layer 80 can be in a range of 3 to 5 μm, which results in single mode lasing operation.

It is generally known that a refractive index (n) of indium phosphate (InP), which is widely used as a backbone material for building a microlaser emitting at near infrared wavelengths, is a function of temperature (T) with $dn/dT=2\times10^{-4}$. [4]. For prior art microlaser designs emitting at near infrared wavelengths, this thermal coefficient can be translated into $d\lambda_e/dT\sim0.1$ nm/K, where $\lambda_e$ is the emission wavelength of the laser[5], which implies that, if $\Delta T$ (temperature change)=50 K, one should observe about $\Delta\lambda_e=5$ nm red-shift in the wavelength of emitted beam 211. Therefore, as shown in FIG. 6B, one would observe a wavelength increase of a few nanometers.

Most microlasers undergo noticeable degradation in output power upon an increase in the temperature of operation because the gain of a microlaser tends to decrease as temperature increases. In accordance with the disclosure, the modified operational conditions of a microlaser, more particularly the changes in the emission wavelength and/or the changes in the intensity of emitted beam 211, can be used to detect an occurrence of an event.

Emitted beam 211 may be transported via a wide variety of transmission media, such as for example, free space optics and optical fiber media, and may be used for providing various types of information depending on the type of application in which the various embodiments described herein are used. For example, in a first application, the information may be a digital bit stream that indicates occurrence or non-occurrence of an event, or carries digital communication data. In a second application, the information pertains to voltage levels and/or current levels present in various elements of a system (for example, on line 216, or on the lines that couple photovoltaic power source 205 to the microlaser).

Furthermore, the microlaser systems described herein can be used in a side variety of environments, such as in an in-vivo environment described above. In another implementation, the system may be integrated into certain structures, such as for example, a wing of an airplane made of a composite material. A suitable transparent epoxy window may be used in such an implementation for propagating emitted beam 211.

All patents and publications mentioned in the specification may be indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The examples set forth above are provided to give those of ordinary skill in the art a complete disclosure and description of how to make and use the embodiments described herein, and are not intended to limit the scope of what the inventors regard as their disclosure. Modifications of the above-described modes for carrying out the disclosure may be used by persons of skill in the relevant arts, and are intended to be within the scope of the following claims.

A number of embodiments of the disclosure have been described. Nevertheless, it will be understood that various modifications may be made without departing from the spirit and scope of the present disclosure. Accordingly, other embodiments are within the scope of the following claims.

LIST OF REFERENCES

[1] A. Scherer, et al. "Systems and methods for optically powering transducers and related transducers," US patent Pub. No. US2011/0044694 A1.
[2] M. Fujita, et al. "Continuous wave lasing in GaInAsP microdisk injection laser with threshold current of 40 μA," Electron. Lett., Vol. 36, pp. 790-791 (2000).
[3] Y. Mo, et al. "Micro-machined gas sensor array based on metal film micro-heater," Sensors and Actuators B, Vol. 79, pp. 175-181 (2001).
[4] R. Ushigome, et al. "GaInAsP microdisk injection laser with benzocyclobutene polymer cladding and its athermal effect," Jpn. J. Appl. Phys., Vol. 41, pp. 6364-6369 (2002).
[5] K. Inoshita and T. Baba, "Fabrication of GaInAsP/InP photonic crystal lasers by ICP etching and control of resonant mode in point and line composite defects," IEEE J. Sel. Top. Quantum Electron., Vol. 9, pp. 1347-1354 (2003).
[6] A. S. Sadek, et al., "Wiring nanoscale biosensors with piezoelectric nanomechanical resonators," Nano Lett., Vol. 10, pp. 1769-1773 (2010).

What is claimed is:

1. A method of operation comprising:
directing light upon a microlaser for optically pumping the microlaser; and
detecting the occurrence of a triggering event based on a change in an optical output of the microlaser, the change in the optical output occurring in response to connecting a photovoltaic power source to the microlaser only upon occurrence of the triggering event, wherein changing the optical output of the microlaser comprises an electrostatic displacement of at least one element of a capacitive assembly comprising two micro-discs separated by an insulating layer, each micro-disc comprising an active layer of the microlaser.

2. The method of claim 1, further comprising:
reducing power consumption by disconnecting the photovoltaic power source from the microlaser during an absence of the triggering event.

3. The method of claim 2, wherein directing light upon the microlaser comprises using a light source to direct a first portion of light upon the microlaser and a second portion of light upon the photovoltaic power source.

4. The method of claim 3, wherein the photovoltaic power source is operative to converting the second portion of light into electrical power, and wherein the microlaser is operative to use the first portion of light to enter a lasing state without using the electrical power of the photovoltaic power source.

5. The method of claim 1, wherein the change in the optical output comprises at least one of a) a change in a wavelength of the optical output of the microlaser and b) a change in an intensity of the optical output of the microlaser.

6. A method of operation comprising:
   directing light upon a microlaser for optically pumping the microlaser; and
   connecting a photovoltaic power source to modify an operational condition of the microlaser only upon occurrence of a triggering event, the modified operational condition indicative of the occurrence of the triggering event, wherein modifying the operational condition of the microlaser comprises an electrostatic displacement of at least one element of a capacitive assembly comprising two micro-discs separated by an insulating layer, each micro-disc comprising an active layer of the microlaser.

7. The method of claim 6, wherein the triggering event is the detection of a substance in a bloodstream.

* * * * *